United States Patent [19]

Andersson

[11] Patent Number: 5,192,472
[45] Date of Patent: Mar. 9, 1993

[54] METHOD FOR PRODUCING A CERAMIC ARTICLE

[75] Inventor: Matts Andersson, Fåker, Sweden

[73] Assignee: Nobelpharma AB, Gothenburg, Sweden

[21] Appl. No.: 729,844

[22] Filed: Jul. 12, 1991

Related U.S. Application Data

[63] Continuation of Ser. No. 483,726, Feb. 23, 1990, abandoned.

[30] Foreign Application Priority Data

Feb. 23, 1989 [SE] Sweden ................................ 8900620

[51] Int. Cl.$^5$ ...................... A61C 13/00; C04B 33/32; B29C 59/00; B29C 33/40
[52] U.S. Cl. ...................................... 264/40.1; 264/16; 264/56; 264/66; 264/129; 264/162; 264/220
[58] Field of Search ...................... 264/16, 19, 56, 60, 264/62, 162, 163, 219, 220, 222, 66, 129, 40.1

[56] References Cited

U.S. PATENT DOCUMENTS

| | | | |
|---|---|---|---|
| 2,271,454 | 1/1942 | Erdle et al. | 18/55 |
| 3,880,971 | 4/1975 | Pantanelli | 264/56 |
| 4,842,454 | 6/1989 | Gustavsson et al. | 409/84 |

FOREIGN PATENT DOCUMENTS

| | | |
|---|---|---|
| 0030850 | 6/1981 | European Pat. Off. . |
| 0107476 | 5/1984 | European Pat. Off. . |
| 449796 | 3/1913 | France . |

Primary Examiner—Jan H. Silbaugh
Assistant Examiner—Christopher A. Fiorilla
Attorney, Agent, or Firm—Pollock, Vande Sande & Priddy

[57] ABSTRACT

A method of producing an article of ceramic material for replacement of a lost substance or tissue in the human body includes making a model having a contour of the article to be produced and positioning in a copying machine the model and a blank from which a tool is to be made. The contour of the model is sensed by sensing devices and transmitted to the blank. The model contour is linearly enlarged by use of mechanical procedures so as to define a linearly enlarged contour on the blank. After the enlarged contour has been defined on the blank, a tool is formed from the blank which has a contour corresponding to the linearly enlarged contour. The ceramic starting material is applied and compacted over the contour of the tool to produce an article with a corresponding enlarged contour. Finally, the article is removed from the tool and is treated in at least one sintering procedure such that the article with the enlarged contour is subjected to linear shrinkage until the size of the article contour corresponds to that of the model contour.

21 Claims, 2 Drawing Sheets

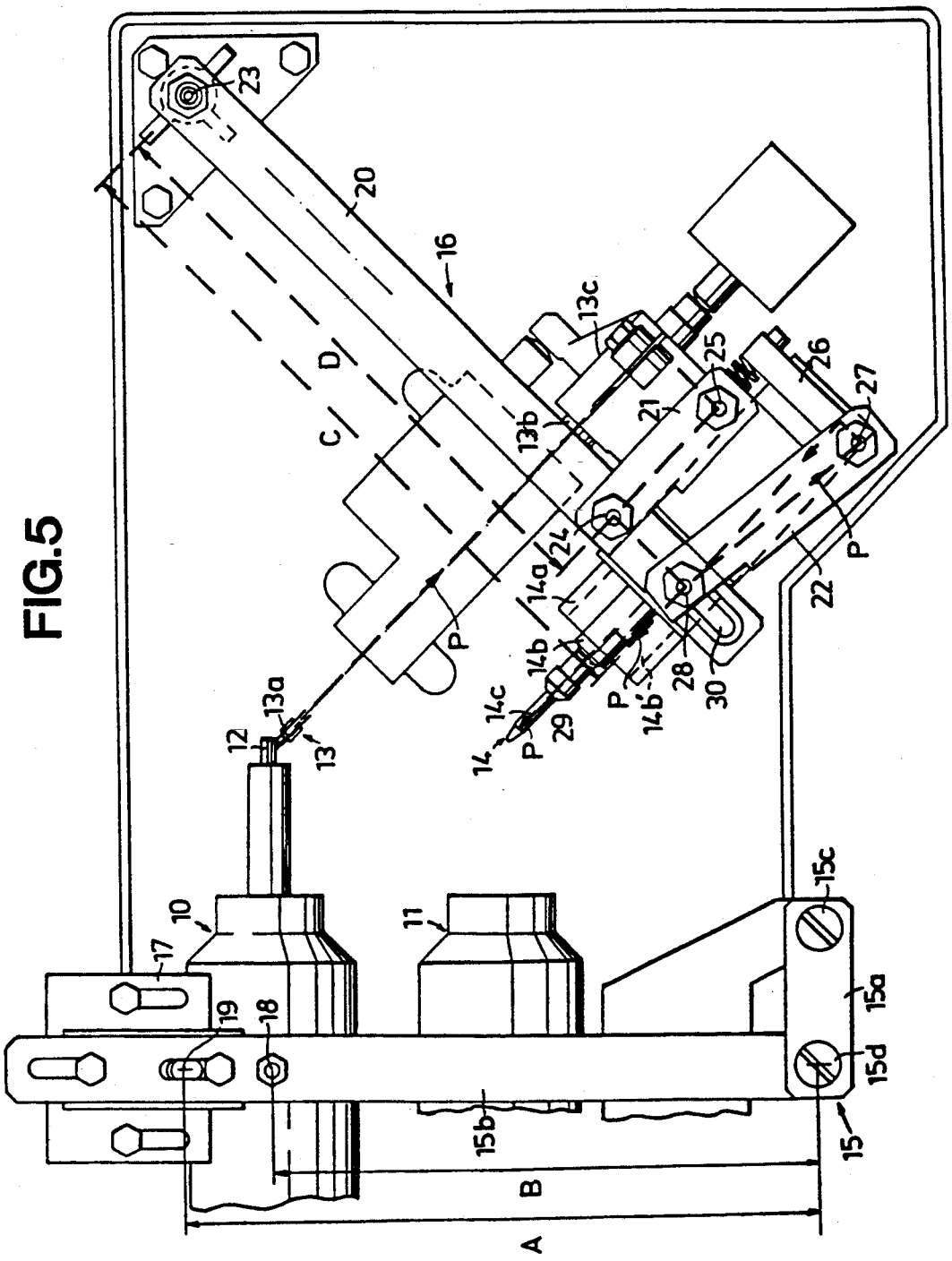

METHOD FOR PRODUCING A CERAMIC ARTICLE

This application is a continuation of Ser. No. 483,726, filed on Feb. 23, 1990, now abandoned.

BACKGROUND OF THE INVENTION

1. Technical Field

The present invention relates to a method for producing a unit which consists of ceramic material and is designed to replace lost substance or tissue in the human body. The method is based on transferring a contour from a preparation model or a place where the replacement is to be carried out to a tool.

2. Prior Art

Various methods are already known for replacing lost substance, for example tooth substance, or tissue with a unit made of ceramic material. In this respect the replacement may be complete in so-called crown treatment or partial in so-called filling treatment. Ceramic material is preferable for many reasons. Among other things, it has a high degree of biocompatibility and affords the possibility of a natural reproduction of color, luster and appearance. In addition, it has very good resistance to various attacking factors. The ceramic units (articles) which are available today in this field have the great disadvantage that they are not sufficiently strong, but instead easily break during use. Flexural strength has in particular proven difficult to satisfy. In addition, the methods by which the unit is produced are based on essentially manual procedures which require great craftsmanship. The ceramic units must in most cases be produced with great accuracy, for example an accuracy of 0.01 mm or less.

SUMMARY OF THE INVENTION

The aim of the present invention is to provide a method for producing a ceramic unit, which solves at least some of the above problems. The feature which can principally be regarded as characterizing the new method is that the model contour in question is transferred in a linearly enlarged state to a part belonging to a tool, on whose enlarged contour ceramic starting material is applied and compacted (compressed). The unit produced in this way is then removed and treated in one or more sintering procedures to carry out linear shrinking until the contour defined by the tool part has essentially the same size as the model contour. In one embodiment a mold cavity is formed with the tool part. The starting material is applied in the cavity and is subjected there to compressive force.

In a preferred embodiment two different sintering stages are used, a pre-sintering procedure and a final sintering procedure. After the pre-sintering the article is given a desired outer form by machining, for example by grinding. After the final sintering the article is individualized, for example by means of applying porcelain to the article and firing it to the desired outer contour and color.

In one proposed embodiment the model contour in question is enlarged by between 16 and 25%, preferably about 20%, and by means of the sintering procedures the article is shrunk by a corresponding percentage. The ceramic starting material introduced into the mold cavity is pressed isostatically or automatically with a high compressive force, for example of about 2000 MPa (about 200 kp/mm$^2$). The pre-sintering is carried out at a temperature of 800–1300° C., while the final sintering is carried out at a temperature of 1100–1600° C.

The above method permits economical production of individually shaped wholly ceramic units/articles with considerably higher strength characteristics, in particular higher flexural strength characteristics than today's ceramic units/articles. For example, the articles made by the present invention method withstand tensile stresses of magnitude which is 3–4 times higher than is possible to achieve with today's articles and methods.

The present method makes it possible to produce, in an economical manner, individual ceramic units for attachment to prepared underlays. By linearly enlarging the model of the prepared underlay and by allowing the enlarged replica (tool/tool part) to be the starting model for the subsequent production, it is possible to achieve complete or very long sintering of the ceramic unit, which affords the better flexural strength characteristics. This has not been possible hitherto.

One preferred embodiment of a method for producing a ceramic unit will be described below with reference to the attached drawings, in which

BRIEF DESCRIPTION OF THE DRAWINGS

FIG. 5 shows a horizontal view of a copying machine by means of which the shape/contour of the model can be transferred linearly enlarged to the press tool part.

DETAILED DESCRIPTION OF THE PREFERRED EMBODIMENT

Figure 1:
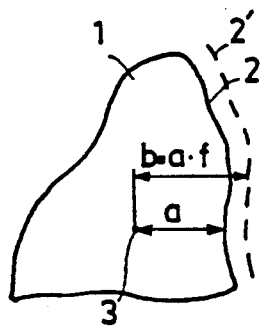
FIG. 1 shows a vertical view of a used model in relation to the linear enlargement which is to be transferred to a press tool part.

FIG. 1 shows a starting model (preparation model) 1 with a contour 2 (for example outer contour) to which the produced unit (in the present case the cap) is to be matched with great accuracy, for example 0.01 mm or less. The center of gravity of the article is indicated by 3 and a given distance from the contour 2 is indicated by a. The linear enlargement f which is to be made of the model contour 2 according to the present invention means that the distance b, which relates to the distance a in the enlarged state, will have the value according to the equation:

$$b = a \cdot f$$

in which f = the enlargement factor.

This enlargement relationship applies to all distances between the center of gravity 3 and the contour 2.

The linearly enlarged contour 2 is transferred to a press tool part 4 which defines a mold cavity 5 in a press tool 6. Ceramic starting material, for example aluminium oxide, is applied in the cavity and is compressed at high pressure, for example 2000 MPa. Pressing procedures which are known in this art can be used in this case, for example isostatic pressing or automatic pressing. Alternatively, slip casting, die casting, injection molding or another compacting method can be used.

The unit 7 thus produced is released or removed from the tool and is pre-sintered in a furnace 8 at about 800-1300°C. The article 7 is then machined to the desired outer shape. The machining can be carried out manually, for example using a grinding machine 9 or another machining device, such as a laser. After machining, final sintering is carried out in the furnace 8 at a temperature of 1100-1600° C. The sintering procedure/sintering procedures is/are known and is/are of the type in which the shrinking of the unit is controlled exactly so as to give a dimension in which the outer contour 2" matches with a high degree of precision the size and shape of the contour 2 of the model 1. After checking, the unit/hood/cap can be individualized by firing conventional porcelain such as dental porcelain in a known manner to give the correct outer contour and correct color.

Figure 3:
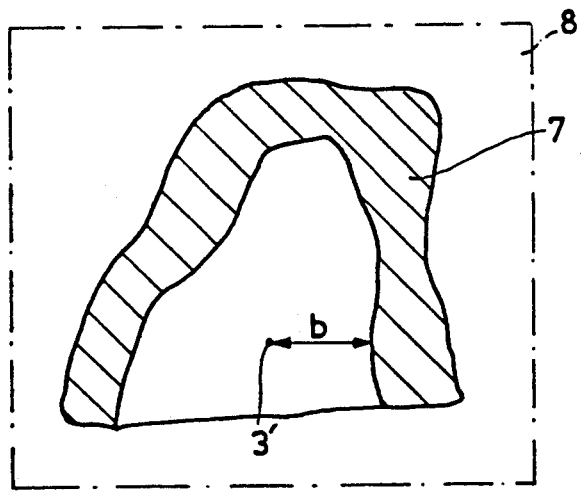
FIG. 3 shows, in vertical section and in principle, the sintering procedure for the ceramic unit.
Figure 4:
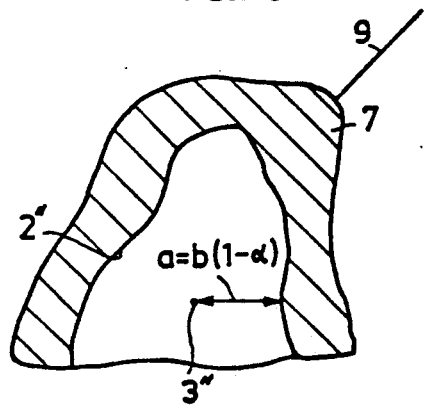
FIG. 4 shows, in vertical section, the machining of the outer contour of a unit produced and enlarged in the press tool.

FIG. 3 shows the enlarged distance b between the center of gravity 3 and the relevant point on the inner surface of the unit 7. In FIG. 4 the shrunk distance a between the center of gravity 3" and the relevant point on the inner wall is obtained as follows:

$a = b(1-\alpha)$ in which $\alpha$ = the shrinkage factor.

Figure 2:
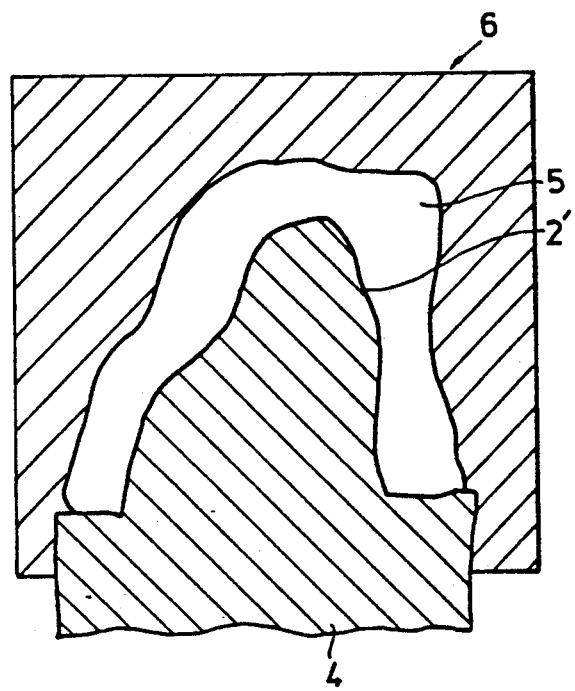
FIG. 2 shows, in vertical section, parts of the press tool comprising, on the one hand, the press tool part with the enlarged contour and, on the other hand, a mold cavity defined by the press tool part.

The production of the tool part with simultaneous transfer of the model contour 2 in a linearly enlarged state 2' can be achieved by using a modified embodiment of the copying machine according to Swedish patent 8601870-2. The modified parts of the machine emerge from FIG. 5. In this known machine, a pair of first units 10 and 11 is rotatably arranged in a housing which is displaceable in the longitudinal direction of the units. The first unit 10 supports the model 3 and the second unit 2 supports in a corresponding manner a blank (not shown in FIG. 5) from which the tool part 4 (see FIG. 2) is to be produced. The copying machine also comprises a second pair of units, here referred to as the third and fourth units 13 and 14. The third unit consists of a detecting member/a needle 13a which senses the contour of the rotating model 12. The fourth unit supports a cutter or another tool for shaping the blank secured on the unit 11.

The first and second pairs of units are designed as longitudinally displaceable in their longitudinal directions towards and away from each other. In the known machine these movements, here called the first longitudinal displacement movements, are of the same size for the units in each pair. According to the present modification, the units in each pair of units will moreover be mutually displaceable in such a way that, during copying, the one unit has a second displacement movement or additional movement besides the first displacement movement. The second displacement movement or additional movement gives the linear enlargement in the copying. The units 10, 11 in the first pair effect the enlargement in the longitudinal direction of the model, and the units 13, 14 in the second pair effect the enlargement in the radial direction of the model. In the preferred embodiment the unit 10 is displaceable relative to the unit 11, and the unit 14 is displaceable relative to the unit 13.

In the case shown, the additional movements are obtained by means of a first linkage system 15 for the units of the first pair and a second linkage system 16 for the units of the second pair. Each linkage system is designed in such a way that the percentage degree of enlargement is adjustable in each case.

The first linkage comprises link arms 15a and 15b. Link arm 15a is rotatably mounted at a point 15c, and the link arms are mounted rotatable with respect to each other at a point 15d. The link arm 15b extends across the parallel units 10, 11 to a bracket 17 which follows the first longitudinal displacement movement of the unit 10. The movement of the bracket is transferred to the end of the link arm 15b, and the link arm 15b in turn transmits its movement to the unit 10 which is mounted displaceable relative to the unit 11 in a manner not shown specially. The transfer to the unit 10 takes place at a point 18. Two distances A and B are shown. A is identical to the distance between the bearing point 15d and a point 19 at which transmission of the movement of the bracket to the link arm 15b takes place. B is the distance between the bearing point 15d and the working point 18. The additional movement of the unit 11 relative to the unit 10 is determined by the relationship A/B. The movement of the unit 10 relative to the unit 11 is braked by means of the linkage system. The point 19 is arranged displaceable in the longitudinal direction of the link arm 15b so that variation of the distance A can be achieved.

The second linkage system 16 comprises a link arm 20 which extends across the parallel units 13 and 14. Link arms 21 and 22 are also included. The member 13a in the unit 13 is longitudinally displaceable in the body of the unit, where it acts on a similarly longitudinally displaceable servo piston 13b. The latter supports a bearing part 13c for the unit 14 which comprises a spindle housing 14a firmly attached to the bearing part 13c. The spindle housing bears a sleeve which is fixed relative to the spindle housing in the rotational direction, but is longitudinally displaceable relative to the spindle housing. A spindle 14b which supports a tool 14c is rotatably mounted in the sleeve but is fixed with respect to the latter in the direction of longitudinal displacement.

The links 20, 21 and 22 are allocated screws or bearing points 23, 24, 25, 27 and 28. Screw 24 is mounted in link 21 and screwed securely in link 20. Screw 25 is mounted in link 21 but is screwed securely at 13c. Screw 28 is mounted in link 22 and is screwed securely in link 20. The screw 28 can be screwed securely at any chosen position in the groove 30 in link 20. The screw 27 is mounted in the link 22 and is screwed securely in a unit 26 which is clamped securely on the abovementioned sleeve. The movement from the member 13a thus passes along the trajectory shown by arrows P.

When 13c moves a certain distance, the point 24 also moves. The link 20 then moves a certain defined angular distance about the bearing 23. The point 28 then moves a distance which is C/D greater than the distance which 24 moves. The enlargement f is thus C/D. The setting of the enlargement is obtained by tightening the screw 28 at a chosen position.

The additional movements for each unit in each pair of units can be effected by using members effecting additional movements other than the mechanically operated linkage system, for example electric motors, hydraulic cylinders, etc.

The invention is not limited to the embodiment shown above by way of example, but can instead be subject to modifications within the scope of the following patent claims.

I claim:

1. A method for producing an article of ceramic material for replacement of lost substance of tissue in the human body, said method comprising the steps of:

a) making a model having a contour of the article to be produced;
b) positioning both said model and a blank from which a tool is made in a copying machine having sensing members and mechanical members;
c) sensing the contour of said model and transferring said contour towards said blank by said sensing members of said copying machine;
d) linearly enlarging said contour transferred towards onto said blank by said mechanical members of said copying machine to provide a linearly enlarged contour for said blank;
e) forming from said blank a tool which has a contour corresponding to said linearly enlarged contour is capable of withstanding high pressures and of maintaining high accuracy;
f) applying and compacting a ceramic starting material over said contour of said tool to produce an article with an enlarged contour; and
g) removing said article from said tool and sintering said article whereby said article linearly shrinks until said article contour corresponds to said model contour.

2. A method according to claim 1, wherein said model contour is a substantially concave contour.

3. A method according to claim 1, wherein said model contour is a substantially convex contour.

4. A method according to claim 1, wherein a mold cavity is formed wherein the ceramic starting material is applied in said mold cavity which is formed between a part of said tool with enlarged contour and another tool part.

5. A method according to claim 4, wherein after removing said article from said tool, but before a final sintering, said article is pre-sintered.

6. A method according to claim 1, wherein after removing said article from said tool, but before the final sintering, said article is pre-sintered.

7. A method according to claim 6, wherein after the pre-sintering said article is given a desired outer shape by manual grinding.

8. A method according to claim 7, wherein said model contour is enlarged by between 16-25%, and wherein corresponding shrinking is carried out in the final sintering procedure.

9. A method according to claim 6, wherein after said final sintering said article is individualized by applying porcelain on said article and firing it to the desired outer contour and color.

10. A method according to claim 9, wherein said model contour is enlarged by between 16-25%, and wherein corresponding shrinking is carried out in the final sintering procedure.

11. A method according to claim 6, wherein the model contour is enlarged by between about 16 to 25% and wherein corresponding shrinking is carried out in the final sintering procedure.

12. A method according to claim 11, wherein the ceramic material applied in the mold cavity is pressed isostatically or automatically at a high compressive force of about 2000 MPa.

13. A method according to claim 6, wherein the ceramic material applied in the mold cavity is pressed isostatically or automatically at a high compressive force of about 2000 MPa.

14. A method according to claim 6, wherein the pre-sintering is carried out at a temperature of between 800–1300° C.

15. A method according to claim 6, wherein the final sintering is carried out at a temperature of 1100–1600° C.

16. A method according to claim 1, wherein the ceramic material applied in the mold cavity is pressed isostatically or automatically at a high compressive force of about 2000 MPa.

17. A method according to claim 16, wherein the pre-sintering is carried out at a temperature of between 800–1300° C.

18. A method according to claim 1, wherein the pre-sintering is carried out at a temperature in the range from about 800° C. to about 1300° C.

19. A method according to claim 18, wherein the final sintering is carried out at a temperature of about 1100° C. to about 1600° C.

20. A method according to claim 18, wherein the final sintering is carried out at a temperature of 1100–1600° C.

21. A method according to claim 1, wherein after the final sintering said article is individualized by applying porcelain on said article and firing it to the desired outer contour and color.

* * * * *